(12) United States Patent
Wang

(10) Patent No.: US 6,723,675 B1
(45) Date of Patent: Apr. 20, 2004

(54) CATALYST FOR THE PRODUCTION OF OLEFIN POLYMERS

(75) Inventor: Chunming Wang, Belle Mead, NJ (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 09/578,273

(22) Filed: May 25, 2000

(51) Int. Cl.$^7$ .................... B01J 31/00; B01J 37/00; C08F 4/02; C08F 4/60; C08F 4/44

(52) U.S. Cl. ............... 502/103; 502/117; 502/152; 502/155; 502/156; 526/161; 526/172

(58) Field of Search ............... 502/103, 117, 502/152, 155, 156; 526/161, 172

(56) References Cited

U.S. PATENT DOCUMENTS

| | | | |
|---|---|---|---|
| 5,418,200 A | 5/1995 | Carney et al. | 502/117 |
| 5,684,100 A | 11/1997 | Carney et al. | 526/160 |
| 5,744,415 A * | 4/1998 | Wenzel | 502/156 |
| 5,814,574 A * | 9/1998 | McNally | 502/156 |
| 5,965,758 A * | 10/1999 | Nabika et al. | 502/103 |
| 5,969,062 A * | 10/1999 | Moll et al. | 502/155 |
| 6,034,022 A * | 3/2000 | McAdon et al. | 502/118 |
| 6,169,051 B1 * | 1/2001 | Mitani et al. | 502/103 |
| 6,175,026 B1 * | 1/2001 | Eisch et al. | 502/117 |
| 6,180,737 B1 * | 1/2001 | Kristen et al. | 502/155 |
| 6,207,773 B1 * | 3/2001 | Ting et al. | 502/117 |
| 6,218,557 B1 * | 4/2001 | Blankenship | 502/117 |
| 6,239,062 B1 * | 5/2001 | Cribbs | 502/103 |
| 6,248,912 B1 * | 6/2001 | Lang et al. | 502/117 |
| 6,255,418 B1 * | 7/2001 | Jolly et al. | 502/117 |
| 6,258,744 B1 * | 7/2001 | Beckhaus et al. | 502/103 |
| 6,271,322 B1 * | 8/2001 | McCullough et al. | 502/117 |
| 6,515,155 B1 * | 2/2003 | Klosin et al. | 502/103 |
| 6,610,627 B2 * | 8/2003 | Murray | 502/155 |
| 2002/0107341 A1 * | 8/2002 | Murray | |
| 2002/0120081 A1 * | 8/2002 | Guan | |
| 2003/0191013 A1 * | 10/2003 | Munoz-Escalante LaFuente et al. | |
| 2003/0195109 A1 * | 10/2003 | Royo et al. | |

FOREIGN PATENT DOCUMENTS

| | | |
|---|---|---|
| CA | 2260003 | 2/1998 |
| EP | 0805142 A2 | 11/1997 |
| WO | WO 96/13529 | 5/1996 |
| WO | WO 98/04570 | 2/1998 |

OTHER PUBLICATIONS

U.S. RE 37,400 E, Canich, Oct. 2001, reissue of USP 5,631,391, issued May 20, 1997, filed Aug. 19, 1993.*
Emrich et al., "The Role of Metallacycles in the Cromium-Catalyzed Trimerization of Ethylene", *Organometallics*, vol. 16, No. 8, Apr. 15, 1997, p. 1511.

Flores et al., {[2–(Dimethylamino)ethyl] cyclopentadienyl}–trichlorotitanium: A New type of Olefin Polymerization Catalyst, *Organometallics*, vol. 13, No. 11, 1994, p. 4140.

Dohring et al, "Donor–Ligand–Substituted Cyclopentadi-enylchromium (III) Complexes: A New Class of Alkene Polymerization Catalyst. 1. Amino–Substituted Systems", *Organometallics* 2000, 19, 388–402.

* cited by examiner

*Primary Examiner*—Mark L. Bell
*Assistant Examiner*—J. Pasterczyk
(74) *Attorney, Agent, or Firm*—Osborne K. McKinney

(57) ABSTRACT

A catalyst composition for the polymerization of olefins is provided which comprises a catalyst compound and a co-catalyst or a support material or both a co-catalyst and a support material, wherein the catalyst compound comprises a transition metal of Group 4, 5 or 6, an organic compound containing at least one lone pair of electrons, a divalent radical and a Lewis basic group having the following formula:

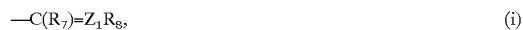

(i)

wherein $R_7$ and $R_8$ are each independently selected from the group consisting of hydrogen and $C_1$–$C_8$ hydrocarbyl groups, and wherein $R_7$ and $R_8$ are not linked or are linked to form a saturated or unsaturated ring; and $Z_1$ is a nitrogen atom or a phosphorus atom, which bonds to M; or

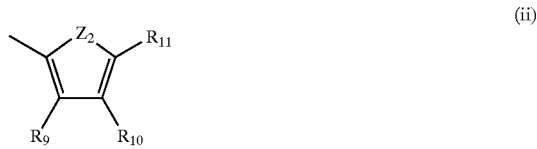 (ii)

wherein:

$Z_2$ is an oxygen atom, a sulphur atom or a selenium atom, which bonds to the transition metal compound; and $R_9$, $R_{10}$ and $R_{11}$ are each independently selected from the group consisting of hydrogen and $C_1$–$C_8$ hydrocarbyl groups, wherein no pair or one pair of substituents selected from $R_9$, $R_{10}$ and $R_{11}$ are linked to form a saturated or unsaturated ring.

15 Claims, No Drawings

CATALYST FOR THE PRODUCTION OF OLEFIN POLYMERS

FIELD OF THE INVENTION

The invention relates to a family of novel catalyst compounds and compositions for the polymerization of olefins. The catalyst compounds and compositions of the invention are especially useful for the production of copolymers of ethylene and alpha olefins, copolymers of ethylene and cyclic olefins, or copolymers of ethylene and alpha olefin-dienes.

BACKGROUND OF THE INVENTION

A variety of metallocenes and single site-like catalysts have been developed to prepare olefin polymers. Metallocenes are organometallic coordination complexes containing one or more π-bonded moieties (i.e., cyclopentadienyl groups) in association with a transition metal atom. Catalyst compositions containing metallocenes and single site-like catalysts are used in the preparation of polyolefins, producing relatively homogeneous copolymers at acceptable polymerization rates while allowing one to tailor closely the final properties of the polymer as desired.

For instance, Döhring et al., "Donor-Ligand-Substituted Cyclopentadienyl-chromium(III) Complexes: A New Class of Alkene Polymerization Catalyst. 1. Amino-substituted Systems" *Organometallics*, 2000, 19, 388–402 discloses complexes which, according to the reference, when treated with MAO, lead to formation of active catalysts for the oligomerization, polymerization and copolymerization of ethylene. One example of such a complex is (cyclo-$C_4H_8NC_2H_4C_5$—$Me_4$)$CrCl_2$ and another is (cyclo-$C_4H_8NC_2H_4C_5Me_4$)$CrMe_2$.

Despite these efforts, a need has remained for catalyst compounds and compositions which enable olefin polymerization reactions to be performed more efficiently, in particular, with enhanced activity. In addition, there has remained a need for catalyst compounds and compositions which enable olefin polymerization reactions to be more closely tailored so as to provide polymer product having desired molecular weight distribution. The catalyst compounds of the present invention, as well as catalyst compositions which contain the catalyst compounds of the present invention, and olefin polymerization reactions which employ the catalyst compounds of the present invention, as described below, satisfy these needs.

SUMMARY OF THE INVENTION

The present invention provides catalyst precursors for use in olefin polymerization reactions. The precursors of the present invention provide high activity for these polymerization reactions, and can be used to produce polyolefins having desired molecular weight distribution, e.g., a narrow molecular weight distribution or a desired range of molecular weight distribution. The present invention also provides catalyst compositions and catalyst systems which comprise the catalyst precursors of the present invention and a co-catalyst, as well as polymerization reactions conducted in the presence of such catalyst precursors, compositions and systems.

The catalyst precursors according to the present invention include those having the formula:

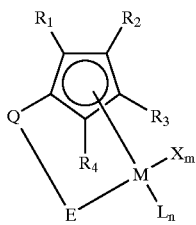

wherein:

$R_1$, $R_2$, $R_3$ and $R_4$ are each independently selected from among hydrogen and $C_1$–$C_8$ hydrocarbyl groups, wherein none, one or two pairs of substituents selected from the group consisting of $R_1$, $R_2$, $R_3$ and $R_4$ are linked to form saturated or unsaturated rings;

M is an atom selected from among the elements of Groups IV, V and VI;

m is 1, 2, 3 or 4;

the or each X is selected from among halide elements, $C_1$–$C_8$ hydrocarbyl groups, $C_1$–$C_8$ alkoxy groups, $C_1$–$C_8$ carboxylate groups and $C_1$–$C_8$ carbamate groups;

n is 1, 2 or 3;

the or each L is an organic compound containing at least one lone pair of electrons;

Q is a divalent radical of the formula $YR_5R_6$, wherein Y is a Group 14 atom, wherein $R_5$ and $R_6$ are each independently selected from among hydrogen and $C_1$–$C_8$ hydrocarbyl groups, and wherein $R_5$ and $R_6$ are not linked or are linked to form a saturated or unsaturated ring;

E is a Lewis basic group having formula (i) or (ii) below:

wherein $R_7$ and $R_8$ are each independently selected from among hydrogen and $C_1$–$C_8$ hydrocarbyl groups, and wherein $R_7$ and $R_8$ are not linked or are linked to form a saturated or unsaturated ring; and $Z_1$ is a nitrogen atom or a phosphorus atom, which bonds to M;

wherein:

$Z_2$ is an oxygen atom, a sulphur atom or a selenium atom, which bonds to M; and $R_9$, $R_{10}$ and $R_{11}$ are each independently selected from among hydrogen and $C_1$–$C_8$ hydrocarbyl groups, wherein no pair or one pair of substituents selected from $R_9$, $R_{10}$ and $R_{11}$ are linked to form a saturated or unsaturated ring.

The invention also provides a catalyst composition comprising a catalyst precursor according to the present invention and an activating co-catalyst, as disclosed below.

The invention also provides a catalyst system comprising a catalyst precursor according to the present invention and an activating co-catalyst as described above, in which the catalyst precursor and the activating co-catalyst are introduced to a reaction system at different locations.

The invention further provides a process for producing an olefin polymer, which comprises contacting at least one olefin monomer under polymerization conditions with a catalyst precursor, and/or a catalyst composition as described above.

The invention further provides olefin polymers, such as ethylene polymers, produced by a process as described in the preceding paragraph, and products, e.g., blow-molded articles, high density films, etc., made from such olefin polymers.

DETAILED DESCRIPTION OF THE INVENTION

In this specification, the term "olefinically unsaturated hydrocarbons" is often represented for convenience by "olefins".

The expression "copolymer" (and other terms incorporating this root), as used herein, refers to polymers containing two or more comonomers, i.e, it encompasses copolymers, terpolymers, etc.

The Group element notation in this specification is as defined in the Periodic Table of Elements according to the IUPAC 1988 notation (IUPAC Nomenclature of Inorganic Chemistry 1960, Blackwell Publ., London). Therein, Group IV, V, XIII, XIV and XV correspond respectively to Groups IVB, VB, IIIA, IVA and VA of the Deming notation (Chemical Rubber Company's Handbook of Chemistry & Physics, 48th edition) and to Groups IVA, VA, IIIB, IVB and VB of the IUPAC 1970 notation (Kirk-Othmer Encyclopedia of Chemical Technology, 2nd edition, Vol. 8, p. 94).

As mentioned above, the catalyst precursor of the present invention has the following formula:

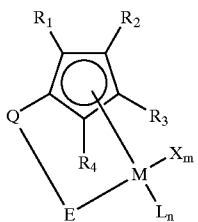

wherein:

$R_1$, $R_2$, $R_3$ and $R_4$ are each independently selected from among hydrogen and $C_1$–$C_8$ hydrocarbyl groups (e.g., preferably methyl), wherein none, one or two pairs of substituents selected from the group consisting of $R_1$, $R_2$, $R_3$ and $R_4$ are linked to form saturated or unsaturated rings (e.g., $R_2$ and $R_3$ are preferably linked to provide an indenyl group);

M is an atom selected from among the elements of Groups IV, V and VI, preferably a transition metal in an oxidation state of +3;

m is 1, 2, 3 or 4;

the or each X is selected from among halide elements, $C_1$–$C_8$ hydrocarbyl groups, $C_1$–$C_8$ alkoxy groups, $C_1$–$C_8$ carboxylate groups and $C_1$–$C_8$ carbamate groups;

n is 1, 2 or 3;

the or each L is an organic compound containing at least one lone pair of electrons;

Q is a divalent radical of the formula $YR_5R_6$, wherein Y is a Group 14 atom, wherein $R_5$ and $R_6$ are each independently selected from among hydrogen and $C_1$–$C_8$ hydrocarbyl groups, and wherein $R_5$ and $R_6$ are not linked or are linked to form a saturated or unsaturated ring;

E is a Lewis basic group having formula (i) or (ii) below:

$$—C(R_7)=Z_1 R_8, \quad (i)$$

wherein $R_7$ and $R_8$ are each independently selected from among hydrogen and $C_1$–$C_8$ hydrocarbyl groups, and wherein $R_7$ and $R_8$ are not linked or are linked to form a saturated or unsaturated ring; and $Z_1$ is a nitrogen atom or a phosphorus atom, which bonds to M;

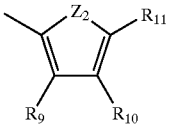

wherein:

$Z_2$ is an oxigen atom, a sulphur atom or a selenium atom, which bonds to M; and $R_9$, $R_{10}$ and $R_{11}$ are each independently selected from among hydrogen and $C_1$–$C_8$ hydrocarbyl groups, wherein no pair or one pair of substituents selected from $R_9$, $R_{10}$ and $R_{11}$ are linked to form a saturated or unsaturated ring.

The hydrocarbyl groups described above are preferably selected from among branched or unbranched alkyl groups.

The catalyst precursor may be prepared by any suitable synthesis method, a number of which will be readily apparent to those of skill in the art.

One useful method of making the catalyst precursor is by reacting a hydroxy aromatic nitrogen compound, which compounds are commercially available, with a metallic deprotonating agent such as an alkyllithium compound in an organic solvent to form the metal salt of the hydroxy aromatic nitrogen compound. The resulting salt may then be reacted with a salt of the desired transition metal, preferably a transition metal halide (i.e., chromium tetrachloride for a chromium-containing catalyst precursor) to form the transition metal catalyst precursor. The catalyst precursor may be isolated by methods well known in the art.

Two or more catalyst precursor compounds may be used in a single catalyst composition to achieve a broadened molecular weight distribution polymer product, if desired.

The activating co-catalyst is capable of activating the catalyst precursor.

Preferred examples of suitable co-catalysts include linear or cyclic (co)oligomeric compounds having a formula (a) $M_{co-cat}R_{12}$, $M_{co-cat}R_{12}R_{13}$, $M_{co-cat}R_{12}R_{13}R_{14}$, or $M_{co-cat}R_{12}R_{13}R_{14}R_{15}$, wherein $M_{co-cat}$ is a metal selected from among alkali metals, alkali earth metals, rare earth metals, aluminum and tin, aluminum being preferred; $R_{12}$, $R_{13}$, $R_{14}$ and $R_{15}$, where present, are each independently selected from among hydrogen, $C_1$–$C_8$ hydrocarbyl groups and $C_1$–$C_8$ alkoxy groups, or (b) $(M_{co-cat}R_{16}O)_p$ $(M_{co-cat}R_{17}O)_q$, wherein $M_{co-cat}$ is a metal selected from among alkali metals, alkali earth metals, rare earth metals, aluminum and tin, aluminum being preferred; $R_{16}$ and $R_{17}$ are each independently selected from among hydrogen and $C_1$–$C_8$ hydrocarbyl groups, and p and q are each independently an integer from 1 to 100. Specific preferred examples of such co-catalysts include the aluminoxanes, in particular MAO, MMAO and IBAO, as well as compounds such as $MgR_{12}R_{13}$, $ZnR_{12}R_{13}$, $SnR_{12}R_{13}R_{14}R_{15}$, $LiR_{12}$, alkali metal alkyls, alkali earth metal alkyls, and aluminum alkyls.

Further examples of preferred co-catalysts which can be used according to the present invention include non-coordinating anion activators. Examples of suitable non-coordinating anion activators include compounds where boron is the anion, e.g., compounds of the formula $B(Ar_1 Ar_2 Ar_3)$, wherein B is boron in a valence state of 3; $Ar_1$, $Ar_2$, and $Ar_3$ are independently selected from among optionally substituted $C_6$–$C_{20}$ aromatic hydrocarbon radicals. Suitable aromatic hydrocarbon radicals include, but are not limited to, phenyl, naphthyl and anthracenyl radicals. These radicals may be unsubstituted or substituted one or more times with one or more substituents. Suitable substituents include, but are not limited to, hydrocarbyl radicals, organometalloid radicals, alkoxy and aryloxy radicals, alkylamido radicals, fluorine, fluorocarbyl radicals and fluorohydrocarbyl radicals. Such substituent(s) may be at any possible position(s) on the aromatic hydrocarbon radical(s), e.g., ortho, meta or para relative to the carbon atom bonded to the anion. One example of such a compound is $B(C_6F_5)_3$. U.S. Pat. No. 5,599,761 discloses some examples of non-coordinating anion compounds which are suitable for use as co-catalysts according to the present invention.

Additional examples of non-coordinating anion activators which are preferred co-catalysts for use according to the present invention include compounds having the formula $[L—H]^+[BAr_1Ar_2Ar_3Ar_4]^*$, wherein:

$[L—H]^+$ is a Bronsted acid, H being a hydrogen atom;

B is boron in a valence state of 3; and $Ar_1$, $Ar_2$, $Ar_3$ and $Ar_4$, are independently selected from among optionally substituted $C_6$–$C_{20}$ aromatic hydrocarbon radicals. Suitable aromatic hydrocarbon radicals include, but are not limited to, phenyl, naphthyl and anthracenyl radicals. These radicals may be unsubstituted or substituted one or more times with one or more substituents. Suitable substituents include, but are not limited to, hydrocarbyl radicals, organometalloid radicals, alkoxy and aryloxy radicals, alkylamido radicals, fluorine, fluorocarbyl radicals and fluorohydrocarbyl radicals. Such substituent(s) may be at any possible position(s) on the aromatic hydrocarbon radical(s), e.g., ortho, meta or para relative to the carbon atom bonded to the anion.

Co-catalysts as described above are known in the art, and can be prepared by those of ordinary skill in the art using any of a variety of known techniques. For instance, aluminoxanes may be prepared in a variety of ways. According to one method of preparing aluminoxanes, a mixture of linear and cyclic aluminoxanes is obtained in the preparation of aluminoxanes from, for example, trimethylaluminum and water. For example, an aluminum alkyl may be treated with water in the form of a moist solvent. Alternatively, an aluminum alkyl, such as trimethylaluminum, may be contacted with a hydrated salt, such as hydrated ferrous sulfate. The latter method comprises treating a dilute solution of trimethylaluminum in, for example, toluene with a suspension of ferrous sulfate heptahydrate. It is also possible to form methylaluminoxanes by the reaction of a tetraalkyldialuminoxane containing $C_2$ or higher alkyl groups with an amount of trimethylaluminum that is less than a stoichiometric excess. The synthesis of methylaluminoxanes may also be achieved by the reaction of a trialkyl aluminum compound or a tetraalkyldialuminoxane containing $C_2$ or higher alkyl groups with water to form a polyalkyl aluminoxane, which is then reacted with trimethylaluminum. Further modified methylaluminoxanes, which contain both methyl groups and higher alkyl groups, i.e., isobutyl groups, may be synthesized by the reaction of a polyalkyl aluminoxane containing $C_2$ or higher alkyl groups with trimethylaluminum and then with water as disclosed in, for example, U.S. Pat. No. 5,041,584.

When the activating co-catalyst is of the formula $AlR_{12}R_{13}R_{14}$, the mole ratio of aluminum atoms contained in the $AlR_{12}R_{13}R_{14}$, compound to total metal atoms contained in the catalyst precursor is generally in the range of from about 2:1 to about 100,000:1, preferably in the range of from about 10:1 to about 100,000:1, and most preferably in the range of from about 50:1 to about 2,000:1. When the activating co-catalyst is of the formula $(AlR_{15}O)_p (Al_{R16}O)_q$, the mole ratio of aluminum atoms contained in the $(AlR_{15}O)_p (AlR_{11}O)_q$ compound to total metal atoms contained in the catalyst precursor is generally in the range of from about 1:1 to about 100,000:1, preferably in the range of from about 5:1 to about 2000:1, and most preferably in the range of from about 50:1 to about 250:1.

The catalyst precursor and the activating co-catalyst may be independently or simultaneously (a) impregnated onto a solid support, (b) in liquid form such as a solution or dispersion, (c) spray dried with a support material, (d) in the form of a prepolymer, or (e) formed in the reactor in-situ during polymerization. Where the catalyst precursor and the activating co-catalyst are to be provided simultaneously, they are preferably first combined and mixed with each other for at least 5 minutes, preferably at least 30 minutes, to provide a composition.

In the case of a supported catalyst composition, the catalyst composition may be impregnated in or deposited on the surface of an inert substrate such as silica, carbon black, polyethylene, polycarbonate porous crosslinked polystyrene, porous crosslinked polypropylene, alumina, thoria, zirconia, or magnesium halide (e.g., magnesium dichloride), and mixtures thereof, such that the catalyst composition is between 0.1 and 90 percent by weight of the total weight of the catalyst composition and the support. These supports preferably have been calcined at a temperature sufficient to remove substantially all physically bound water. Conventional techniques, such as those disclosed in U.S. Pat. No. 4,521,723, can be employed for impregnating the catalyst composition onto a catalyst support.

A preferred support material is a silica material. For example, some such materials are described in U.S. Pat. No. 5,264,506. Desirably, the silica support has an average particle size of from about 60 to 200 (preferably about 70 to 140) microns; no more than about 30 percent by weight silica should have a particle size below about 44 microns. Further, the silica support has an average pore diameter of greater than about 100 Angstrom units, preferably greater than about 150 Angstrom units. It is also desirable for the silica support to have a surface area greater than about 200 square meters per gram. The support should be dry, that is, free of adsorbed water. Drying of the silica is carried out by heating it at a temperature of from about 100 to 800 degrees C., e.g., about 600 degrees C.

Spray-drying may be effected by any spray-drying method known in the art. Spray-drying can be useful to provide catalysts having a narrow droplet size distribution (and resulting narrow particle size distribution) for efficient use of the catalyst and to give more uniform pellets and better performance, in addition to having beneficial morphology.

For example, one example of a suitable spray-drying method comprises atomizing a solution, suspension or dispersion of the catalyst and/or the activating co-catalyst, optionally together with a filler, and optionally with heating of the solution, suspension or dispersion. Atomization is accomplished by means of any suitable atomizing device to form discrete spherically shaped particles. Atomization is preferably effected by passing the slurry through the atomizer together with an inert drying gas, i.e., a gas which is nonreactive under the conditions employed during atomization. An atomizing nozzle or a centrifugal high speed disc can be employed to effect atomization, whereby there is created a spray or dispersion of droplets of the mixture. The volumetric flow of drying gas, if used, preferably considerably exceeds the volumetric flow of the slurry to effect atomization of the slurry and/or evaporation of the liquid medium. Ordinarily the drying gas is heated to a temperature as high as about 160 degrees C. to facilitate atomization of the slurry; however, if the volumetric flow of drying gas is maintained at a very high level, it is possible to employ lower temperatures. Atomization pressures of from about 1 psig to 200 psig are suitable. Some examples of suitable spray-drying methods include those disclosed in U.S. Pat. Nos. 5,290,745, 5,652,314, 4,376,062, 4,728,705, 5,604,172, 5,306,350 and 4,638,029.

Another type of suitable spray-drying method comprises forming a liquid mixture comprising a nonvolatile materials fraction, a solvent fraction and at least one compressed fluid; and spraying the liquid mixture at a temperature and pressure that gives a substantially decompressive spray by passing the mixture through an orifice into an environment suitable for forming solid particulates by solvent evaporation. For example, such a method is disclosed in U.S. Pat. No. 5,716,558.

In general, spray-drying produces discrete, substantially round, abrasive resistant particles with relatively narrow particle size distribution. By adjusting the size of the orifices of the atomizer employed during spray drying, it is possible to obtain particles having desired average particle size, e.g., from about 5 micrometers to about 200 micrometers. The particles recovered from the spray drying step can optionally be decarboxylated by heating the particles, e.g., as disclosed in U.S. Pat. No. 5,652,314.

As mentioned above, catalyst precursor and/or activating co-catalyst may be in the form of a prepolymer. Such prepolymers can be formed in any suitable manner, e.g., by forming one or more polymer or copolymer (which may be the same or different from the polymer(s) and/or copolymer (s) to be collected in the reactor) in the presence of the catalyst precursor and/or activating co-catalyst. For example, processes which provide catalyst precursor and/or activating co-catalyst attached to and at least partially covered by polymeric and/or copolymeric material may be suitable.

The catalyst composition may be used for the polymerization of olefins by any suspension, solution, slurry, or gas phase process, using known equipment and reaction conditions, and is not limited to any specific type of reaction system. Such polymerization can be conducted in a batchwise mode, a continuous mode, or any combination thereof. Generally, suitable olefin polymerization temperatures are in the range of from about 0 degrees C. to about 200 degrees C. at atmospheric, subatmospheric, or superatmospheric pressures.

Preferably, gas phase polymerization is employed, at superatmospheric pressure in the range of from about 1 to about 1000 psi, preferably 50 to 400 psi, most preferably 100 to 300 psi, and at temperatures in the range of from about 30 degrees C. to about 130 degrees C., preferably about 65 degrees C. to about 110 degrees C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally fully or partially condensed as disclosed in U.S. Pat. Nos. 4,543,399, 4,588,790, 5,352,749 and 5,462,999, and recycled to the reactor. Product is withdrawn from the reactor and make-up monomer is added to the recycle stream. As desired for temperature control of the system, any gas inert to the catalyst composition and reactants may also be present in the gas stream. In addition, a fluidization aid such as carbon black, silica, clay, or talc may be used, as disclosed in U.S. Pat. No. 4,994,534.

Slurry or solution polymerization processes may utilize subatmospheric or superatmospheric pressures and temperatures in the range of from about 40 degrees C. to about 110 degrees C. Useful liquid phase polymerization reaction systems are known in the art, e.g., as described in U.S. Pat. No. 3,324,095, U.S. Pat. No. 5,453,471, U.S. Pat. No. 5,834,571, WO 96/04322 (PCT/US95/09826) and WO 96/04323 (PCT/US95/09827). Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. Preferably, reaction medium containing the olefin polymer product and unreacted olefin monomer is withdrawn continuously from the reactor. Olefin polymer product is separated, and unreacted olefin monomer is recycled into the reactor.

Polymerization may be carried out in a single reactor or in two or more reactors in series. In a preferred aspect of the invention, e.g., where a broader molecular weight distribution is desired, tandem reactors are employed (i.e., two or more reactors in series), and two or more of the reactors each have a unique set of reaction conditions, i.e., one or more reaction condition (e.g., which affects polymer molecular weight) is different in one reactor relative to one or more other reactor.

Polymerization is preferably conducted substantially in the absence of catalyst poisons. Organometallic compounds may be employed as scavenging agents for removal of poisons, when necessary, to increase catalyst activity. Examples of scavenging agents include metal alkyls, preferably aluminum alkyls, most preferably triisobutylaluminum.

Conventional adjuvants may be included in the process, provided they do not interfere with the operation of the catalyst composition in forming the desired polyolefin. Hydrogen or a metal or non-metal hydride, e.g., a silyl hydride, may be used as a chain transfer agent in the process. Hydrogen may be used in amounts up to about 10 moles of hydrogen per mole of total monomer feed.

Other conventional additives may be included in the process, provided they do not interfere with the operation of the catalyst composition in forming the desired polyolefin. For example, other additives which may be introduced into one or more streams entering polymer formulation include antioxidants, coupling agents, ultraviolet absorbers or stabilizers, antistatic agents, pigments, dyes, nucleating agents, reinforcing fillers or polymer additives, slip agents, plasticizers, processing aids, lubricants, viscosity control agents, tackifiers, anti-blocking agents, surfactants, extenders oils, metal deactivators, voltage stabilizers, flame retardant fillers and additives, crosslinking agents, boosters, and catalysts, and smoke suppressants. Fillers and additives can be added in amounts ranging from less than about 0.1 to more than about 200 parts by weight for each 100 parts by weight of the base resin, for example, polyethylene.

Examples of antioxidants are: hindered phenols such as tetrakis[methylene(3,5-di-tert-butyl-4-hydroxyhydrocinnamate)]methane, bis[(beta-(3,5-di-tert-butyl4-hydroxybenzyl)-methyl-carboxyethyl)]sulphide, 4,4'-thiobis(2-methyl-6-tert-butylphenol), 4,4'-thio-bis(2-tert-butyl-5-methyl-phenol), 2,2'-thiobis(4-methyl-6-tert-butylphenol), and thiodiethylene bis(3,5-di-tert-butyl-4-hydroxy)hydrocinnamate; phosphites and phosphonites such as tris(2,4-di-tert-butylphenyl) phosphite and di-tert-butylphenyl-phosphonite; thio compounds such as dilaurylthiodipropionate, dimyristylthiodipropionate, and distearylthiodipropionate; various siloxanes; and various amines such as polymerized 2,2,4-trimethyl-1,2-dihydroquinoline. Antioxidants can be used in amounts of about 0.1 to about 5 parts by weight per 100 parts by weight of polyethylene.

Olefin polymers and copolymers that may be produced according to the invention include, but are not limited to, ethylene homopolymers, homopolymers of linear or branched higher alpha-olefins containing 3 to about 20 carbon atoms, and copolymers of olefin (preferably ethylene) and (a) higher alpha-olefins, (b) cyclic olefins or (c) alpha olefin-dienes. Suitable higher alpha-olefins include, for example, propylene, 1-butene, 1-pentene, 1-hexene, 4-methyl-1-pentene, 1-octene, and 3,5,5-trimethyl-1-hexene. Suitable cyclic olefins include, for example, norbornene. Suitable alpha olefin-dienes include linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, vinyl cyclohexene, dicyclopentadiene, butadiene, isobutylene, isoprene, ethylidene norbornene and the like.

Aromatic compounds having vinyl unsaturation such as styrene and substituted styrenes, and polar vinyl monomers such as acrylonitrile, maleic acid esters, vinyl acetate, acrylate esters, methacrylate esters, vinyl trialkyl silanes and the like may be polymerized according to the invention as well.

Specific olefin polymers that may be made according to the invention include, for example, polyethylene, higher olefins, e.g., polypropylene, ethylene/higher olefin, e.g., propylene rubbers (e.g., EPR's), ethylene/higher olefin, e.g. propylene/diene terpolymers (e.g., EPDM's), ethylene/higher olefin, e.g., propylene/cyclic olefin terpolymers, polybutadiene, polyisoprene and the like.

Polymers produced by methods according to the present invention can be crosslinked by adding a crosslinking agent to the composition or by making the resin hydrolyzable, by adding hydrolyzable group. Suitable cross-linking agents are organic peroxides such as dicumyl peroxide; 2,5-dimethyl-2,5-di(t-butylperoxy)hexane; t-butyl cumyl peroxide; and 2,5-dimethyl-2,5-di(t-butylperoxy)hexane-3. Dicumyl peroxide is preferred. Hydrolyzable groups can be added to polymers produced by methods according to the present invention, for example, by copolymerizing ethylene with an ethylenically unsaturated compound having one or more —Si(OR)$_3$ groups such as vinyltrimethoxy-silane, vinyltriethoxysilane, and gamma-methacryloxypropyltrimethoxysilane or grafting these silane compounds to the resin in the presence of the aforementioned organic peroxides. The hydrolyzable resins are then crosslinked by moisture in the presence of a silanol condensation catalyst such as dibutyltin dilaurate, dioctyltin maleate, dibutyltin diacetate, stannous acetate, lead naphthenate, and zinc caprylate. Dibutyltin dilaurate is preferred.

Examples of hydrolyzable copolymers and hydrolyzable grafted copolymers are ethylene/vinyltrimethoxy silane copolymer, ethylene/gamma-methacryloxypropyltrimethoxy silane copolymer, vinyltrimethoxy silane grafted ethylene/ethyl acrylate copolymer, vinyltrimethoxy silane grafted linear low density ethylene/1-butene copolymer, and vinyltrimethoxy silane grafted low density polyethylene.

The present invention enables production of polymer product, and articles formed of such product, having desirable polydispersity index (defined as the ratio of the weight average molecular weight of the polymer to the number average molecular weight of the polymer ($M_w/M_n$)), melt index (determined, e.g., according to ASTM D-1238—Condition E), flow index (determined, e.g., according to ASTM D-1238—Condition F), melt flow ratio (i.e., the ratio of flow index to melt index), density (determined, e.g., according to ASTM D-1505), bulk density (determined, e.g., according to ASTM D-1895—Method B), unsaturation (determined, e.g., using an infrared spectrophotometer, such as a Perkin Elmer Model 21), haze (determined, e.g., according to ASTM D1003-61—Procedure B), gloss (determined, e.g., according to ASTM D2457-70), rheological properties (e.g., via dynamic oscillatory shear experiments conducted with a Weissenberg Rheogoniometer commercially available from TA Instruments.), melt strength behavior, shear thinning behavior, relaxation spectrum index, crystallizable chain length distribution index (determined, e.g., using Temperature Rising Elution Fractionation (TREF), as described in Wild et al., J. Polymer Sci. Poly. Phys. Ed., Vol. 20, p. 441 (1982), compositional homogeneity, ratio of long chain branches to main chain carbon atom, production rate, morphology, avoidance of chips and chunks, avoidance of process upsets, avoidance of particle agglomeration, viscosity, heat of fusion, branching (determined, e.g., by Carbon 13 NMR), and/or short chain branch frequency, (determined, e.g., by infrared spectroscopy as described by Blitz and McFaddin in J. Appl. Pol. Sci., 1994,51,13).

Polymers produced according to the present invention can be used in a variety of applications, representative examples including, e.g., blow-molded articles, high-density films, etc.

The following examples further illustrate the invention.

EXAMPLES:

Materials

Methylalumoxane (MAO) was purchased from the Albemarle Corporation and had a nominal concentration of 3.2 mol(Al)/L. Modified methylalumoxane (MMAO) was purchased from the Akzo Corporation and had a nominal concentration of 1.8 mol(Al)/L. Isobutylalumoxane (IBAO) was purchased from Akzo and had a nominal concentration of 0.98 mol (Al)/L.

Example 1

Synthesis of Catalyst Precursor, 5-[(2-Pyridyl) methyl)]-1,2,3,4-tetramethylcyclopentadienyl Chromium (III) Dichloride (Compound I)

a) Preparation of 5-[(2-Pyridyl)methyl)]-1,2,3,4-tetramethylcyclopentadiene

Lithium tetramethylcyclopentadienyl (10.1 g, 78.8 mmol) was suspended in THF (100 mL) in a 200 cc Schlenk flask and cooled in a dry ice acetone bath. Into this flask was added dropwise a hexane (20 mL) solution of 2-picolyl chloride (10.0 g, 78.4 mmol). The resulting suspension was warmed to room temperature gradually and stirred overnight. Solvent was removed under vacuum and the resulting residue was extracted with hexane (2×30 mL) and filtered, removal of hexane via vacuum resulting in a yellow oil (yield, 17.6 g).

b) Preparation of Lithium, 5-[(2-Pyridyl)methyl)]-1,2,3,4-tetramethylcyclopentadienyl The above oil was redissolved into hexane (100 cc) in a 200 cc Schlenk flask and cooled in a dry ice acetone bath. BuLi (13.2 mL, 2.5 M in hexane, 33 mmol) was added dropwise, the resulting suspension was warmed to room temperature gradually and stirred overnight. The resulting yellow suspension was filtered and washed with hexane (2×10 mL) and dried under vacuum to yield a yellow-brown solid (yield, 7.8 g).

c) Preparation of 5-[(2-Pyridyl)methyl)]-1,2,3,4-tetramethylcyclopentadienyl Chromium (III) Dichloride (Compound I)

$CrCl_3(THF)_3$ (from Aldrich, 3.0 g, 7.8 mmol) was suspended in THF (40 mL) in a 200 cc Schlenk flask and cooled in a dry ice acetone bath. Into this flask was added dropwise via a cannula a THF (20 mL) solution of lithium, 5-[(2-pyridyl)methyl)]-1,2,3,4-tetramethylcyclopentadienyl (1.7 g, 7.8 mmol). The resulting brownish suspension was warmed to room temperature gradually (a dark-blue solid appeared upon warm-up) and stirred overnight. It was filtered and washed with 10 cc hexane and dried under vacuum to result in a bright-blue solid (1.5 g). THF was removed and the resulting residue was extracted with $CH_2Cl_2$ and filtered again, removal of $CH_2Cl_2$ further resulted in 1.0 g of product. Total yield 2.5 g. +APCl/MS spectrum from THF volatilized: [Cr*Cl]+, calculated m/e 299.05, [Cr*Cl-THF]+, calculated m/e 371.11; [Cr*Cl]+, found m/e 298.9, [Cr*Cl-THF]+, found m/e370.9.

Example 2

Synthesis of Catalyst Precursor, 5-[(2-Pyridyl) methyl)]-1,2,3,4-tetramethylcyclopentadienyl Vanadium (III) Dichloride (Compound II)

$VCl_3(THF)_x$ (from Strem, 3.4 g, 10.1 mmol) was suspended in $CH_2Cl_2$ (40 mL) in a 200 cc Schlenk flask and cooled in a dry ice acetone bath. Into this flask was added dropwise via a cannula a $CH_2Cl_2$ (20 mL) solution of lithium, 5-[(2-pyridyl)methyl)]-1,2,3,4-tetramethylcyclopentadienyl (2.2 g, 10.0 mmol). The resulting brownish-suspension was warmed to room temperature gradually (which changed into a dark-purple color upon warm-up) and stirred overnight. After filtration, the solvent was removed under vacuum and the resulting solid was washed with hexane (2×10 cc) and dried under vacuum. Yield 4.24 g, brown solid. +APCl/MS spectrum from THF volatilized: [V*Cl]+, calculated m/e 298.06, [Cr*Cl-THF]+, calculated m/e 370.11, [V*Cl]+, found m/e 297.9, [V*Cl-THF]+, found m/e370.0.

Example 3

Synthesis of Catalyst Precursor, 5[(2-Pyridyl) methyl)]-1,2,3,4-tetramethylcyclopentadienyl Titanium (III) Dichloride (Compound III)

$TiCl_3(THF)_3$ (from Aldrich, 3.48 g, 9.1 mmol) was suspended in THF (40 mL) in a 200 cc Schlenk flask and cooled in a dry ice acetone bath. Into this flask was added dropwise via a cannula a THF (20 mL) solution of lithium, 5-[(2-pyridyl)methyl)]-1,2,3,4-tetramethylcyclopentadienyl (2.0 g, 9.2 mmol). The resulting suspension was warmed to room temperature gradually and stirred overnight. It was filtered and washed with 10 cc hexane and dried under vacuum to result in a brownish-red solid (1.7 g). +APCl/MS spectrum from THF volatilized: [Ti*Cl-THF]+, calculated m/e 367.11; [Ti*Cl-THF]+, found m/e367.0.

Example 4

Synthesis of Catalyst Precursor, (2-Pyridylmethyl)-cyclopentadienyl Chromium (III) Dichloride (Compound IV)

a) Preparation of (2-Pyridylmethyl)-cyclopentadiene

Lithium cyclopentadienyl (7.3 g, 102 mmol) was suspended in THF (150 mL) in a 300 cc Schlenk flask and cooled in a dry ice acetone bath. Into this flask was added slowly a THF (60 mL) solution of 2-picolyl chloride (13 g, 102 mmol). The resulting suspension was warmed to room temperature gradually and stirred overnight. Solvent was removed under vacuum and the resulting residue was extracted with hexane (2×30 mL) and filtered, removal of hexane via vacuum resulting in a redish-brown oil (yield, 6.8 g).

b) Preparation of Lithium (2-Pyridylmethyl)-cyclopentadienyl

The above oil (6.8 g, 43 mmol) was redissolved into hexane (40 cc) in a 200 cc Schlenk flask and cooled in a dry ice acetone bath. BuLi (17.2 mL, 2.5 M in hexane, 43 mmol) was added dropwise, the resulting suspension was warmed to room temperature gradually and stirred overnight. The resulting suspension was filtered and washed with diethyl ether (2×10 mL) and dried under vacuum to yield a dark-brown solid (yield, 7.1 g).

c) Preparation of (2-Pyridylmethyl)-cyclopentadienyl Chromium (III) Dichloride $CrCl_3(THF)_3$ (from Aldrich, 3.0 g, 7.8 mmol) was suspended in THF (25 mL) in a 200 cc Schlenk flask and cooled to 46° C. Into this flask was added dropwise via a cannula a THF (20 mL) solution (cooled at −46 degrees C.) of lithium (2-pyridylmethyl)-cyclopentadienyl (1.4 g, 8.4 mmol). The resulting brownish suspension was warmed to room temperature gradually (a dark-blue solid appeared upon warm-up) and stirred overnight. It was filtered and washed with 10 cc hexane and dried under vacuum to result in a blue solid (0.7 g). THF was removed and the resulting residue was extracted with $CH_2Cl_2$ and filtered again, removal of $CH_2Cl_2$ further resulted in 1.6 g of product. Total yield 2.3 g.

Example 5

Synthesis of Catalyst Precursor, 1-(2-Pyridylmethyl)-indenyl Chromium (III) Dichloride (Compound V)

a) Preparation of (2-Pyridylmethyl)-indene

Lithium indenyl (3.0 g, 24.6 mmol) was suspended in THF (20 mL) in a 300 cc Schlenk flask and cooled in a dry ice acetone bath. Into this flask was added slowly a THF (15 mL) solution of 2-picolyl chloride (3.13 g, 24.6 mmol). The resulting suspension was warmed to room temperature gradually and stirred overnight. Solvent was removed under vacuum and the resulting residue was extracted with ether (2×30 mL) and filtered, removal of ether via vacuum resulting in a dark-brown oil (yield, 4.0 g).

b) Preparation of Lithium (2-Pyridylmethyl)-indenyl

The above oil (4.0 9, 19 mmol) was redissolved into THF/hexane (15cc/15cc) in a 200 cc Schlenk flask and cooled in a dry ice acetone bath. BuLi (8.0 mL, 2.5 M in hexane, 20 mmol) was added dropwise, the resulting suspension was warmed to room temperature gradually and stirred overnight. The resulting suspension was filtered and washed with hexane (2×15 mL) and dried under vacuum to yield a purple solid (yield, 4.2g)

c) Preparation of (2-Pyridylmethyl)-indenyl Chromium (III) Dichloride $CrCl_3(THF)_3$ (from Aldrich, 3.0 g, 7.8 mmol) was suspended in THF (25 mL) in a 200 cc Schlenk flask and cooled to −46° C. Into this flask was added dropwise via a cannula a THF (20 mL) solution (cooled at −46 degrees C.) of lithium (2-pyridylmethyl)-indenyl (1.7 g, 8 mmol). The resulting suspension was warmed to room temperature gradually (a dark-green solid appeared upon warm-up) and stirred overnight. It was filtered and washed with 10 cc hexane and dried under vacuum to result in a dark green-yellow solid (1.15 g). THF was removed and the resulting residue was extracted with $CH_2Cl_2$ and filtered again, removal of $CH_2Cl_2$ further resulted in 1.65 g of product. Total yield 2.8 g.

Example 6

Synthesis of Catalyst Precursor, 5-[(2-Quinolinyl)methyl]-2,3,4-tetramethylcyclopentadienyl Chromium (III) Dichloride (Compound VI)

a) Preparation of 5-[(2-Quinolinyl)methyl]-1,2,3,4-tetramethylcyclopentadiene

Lithium tetramethylcyclopentadienyl (7.8 g, 60.8 mmol) was suspended in THF (100 mL) in a 300 cc Schlenk flask and cooled in a dry ice acetone bath. Into this flask was added dropwise a hexane (20 mL) solution of 2-chloromethyl quinoline (10.0 g, 59 mmol). The resulting suspension was warmed to room temperature gradually and stirred overnight. Solvent was removed under vacuum and the resulting residue was extracted with hexane (2×30 mL) and filtered, removal of hexane via vacuum resulting in a brown oil (yield, 14 g).

b) Preparation of Lithium 5-[(2-Quinolinyl)methyl]-1,2,3,4-tetramethylcyclopenta-dienyl The above oil was redissolved into hexane (200 cc) in a 500 cc Schlenk flask and cooled in a dry ice acetone bath. BuLi (12 mL, 2.5 M in hexane, 30 mmol) was added dropwise, the resulting suspension was warmed to room temperature gradually and stirred overnight. The resulting yellow suspension was filtered and washed with hexane (3×10 mL) and dried under vacuum to yield a dark solid (yield, 10.7 g )

c) Preparation of 5-[(2-Quinolinyl)methyl]-1,2,3,4-tetramethylcyclopentadienyl Chromium (III) Dichloride (Compound VI)

$CrCl_3(THF)_3$ (from Aldrich, 3.0 g, 7.8 mmol) was suspended in THF (25 mL) in a 200 cc Schlenk flask and cooled at −46° C. Into this flask was added dropwise via a cannula a THF (15 mL) solution (cooled at −46 degrees C.) of lithium 5-[(2-quinolinyl)methyl]-1,2,3,4-tetramethylcyclopentadienyl (2.1 g, 7.8 mmol). The resulting dark suspension was warmed to room temperature gradually (a dark-blue solid appeared upon warm-up) and stirred overnight. It was filtered and washed with 10 cc hexane and dried under vacuum to result in a blue-green solid (1.5 g). THF was removed and the resulting residue was extracted with $CH_2Cl_2$ and filtered again, removal of $CH_2Cl_2$ further resulted in 0.7 g of product. Total yield 2.2 g. +APCl/MS spectrum from THF volatilized: [Cr*Cl]+, calculated m/e 349.07, [Ti*Cl−THF]+, calculated m/e 421.13; [Cri*Cl]+, found m/e 348.9, [Cr*Cl−THF]+, found m/e421.0.

Example 7

Synthesis of Catalyst Precursor, 5-[(2-Quinolinyl)methyl]-1,2,3,4-tetramethylcyclopentadienyl Vanadium (III) Dichloride (Compound VII)

$VCl_3(THF)_x$ (from Strem, 3.0 g, 8.9 mmol) was suspended in THF (30 mL) in a 200 cc Schlenk flask and cooled at −46° C. Into this flask was added dropwise via a cannula a THF (20 mL) solution (cooled at −46 degrees C.) of lithium (2-quinolinylmethyl)-tetramethylcyclopentadienyl (2.8 g, 10.4 mmol). The resulting dark suspension was warmed to room temperature gradually (a dark-blue solid appeared upon warm-up) and stirred overnight. It was filtered and then THF was removed, the resulting residue was extracted with $CH_2Cl_2$ and filtered again, removal of $CH_2Cl_2$ resulted in 1.8 g of dark solid. Total yield 2.2 g.

Example 8

Ethylene Polymerization 500 cc hexane and a scavenger were added into a 1 L stainless-steel reactor (Fluitron®) which had been dried by flowing nitrogen through it while it was held at 100 degrees C. for at least 1 hour (h.), it was passivated at least for 0.5 h. Next, ethylene was introduced into the reaction at 110 psi total pressure and the temperature was allowed to equilibrate at 65 degrees C. The desired amount of MAO (in toluene, or MMAO in heptane) preactivated catalyst was injected using a pressure-proof syringe. The pressure in the reaction was kept constant by supplying ethylene and the temperature was maintained at 85 degrees C. through jack-cooling. After 0.5 hour, the polymerization was stopped and the polymer was taken out from the reactor and dried first overnight at ambient temperature and further dried at 50 degrees C. under vacuum. The results are shown in Tables 1 and 2.

TABLE 1

Ethylene polymerization results at 85 degree C.

| Run | Catalyst | [M] μmol | Co-cat | Al/M | C2 Partial (psi) | Time (h) | Yield (g) | Activity (kg/mmol/h/100 psi C2) |
|---|---|---|---|---|---|---|---|---|
| 1 | I | 1 | MAO | 200 | 100 | 0.5 | 52 | 110 |
| 2 | I | 0.5 | MMAO-3A | 300 | 100 | 0.5 | 60 | 215 |
| 3 | II | 1.2 | MAO | 200 | 100 | 0.5 | 91 | 135 |
| 4 | III | 1.7 | MAO | 300 | 100 | 0.5 | 42 | 43 |
| 5 | IV | 5.7 | MAO | 210 | 100 | 0.5 | 45 | 15 |
| 6 | V | 1 | MAO | 300 | 100 | 0.5 | 27 | 45 |
| 7 | VI | 1 | MAO | 100 | 100 | 1.5 | 62 | 38 |
| 8 | VII | 1 | MAO | 100 | 100 | 0.5 | 20 | 37 |

[M] = catalyst loading, micromol
Al/M = molar ratio Al/M

TABLE 2

Analytical Data For Runs 1–8

| Run | Tm (° C.)[a] | Density (g/cc) | Mw (×10$^{-3}$)[b] | MWD |
|---|---|---|---|---|
| 1 | 130 | 0.954 | 230 | 5.8 |
| 3 | 132 | 0.970 | 30 | 3.0 |
| 4 | 133 | >0.970 | 16 | 2.3 |
| 5 | 132 | 0.966 | too high | — |
| 6 | 133 | 0.955 | 135 | 10.6 |
| 7 | 134 | 0.946 | 238 | 2.3 |
| 8 | 125 | 0.943 | 94 | 2.6 |

[a]Determined by DSC, 2$^{nd}$ heat
[b]Determined by GPC

It is significant to note that in the above examples, promoters for preventing extensive reduction of the metal in the catalyst are not required, although such promoters can be used if desired. In the past, vanadium catalysts have typically required a promoter to prevent extensive reduction of the vanadium, e.g., from an oxidation state of +4 to +2, such promoters including, e.g., CBr$_4$ or CCl$_4$.

Example 9

Ethylene/1-hexene Copolymerization Using Compound I

The polymerization run procedures were identical to those of Example 8 except that the desired amounts of 1-hexene were added. The polymerization results and analytical data are shown in Tables 3 and 4.

TABLE 3

1-Hexene/Ethylene Copolymerization Results using compound I

| Run | [M] μmol | Co-cat | Al/M | 1-Hexene (cc) | Time (h) | Yield (g) | Activity (kg/mmol/h/100 psi C2) |
|---|---|---|---|---|---|---|---|
| 9 | 1 | MMAO | 90 | 0 | 0.5 | 65 | 120 |
| 10 | 1 | MMAO | 90 | 20 | 0.5 | 31 | 62 |
| 11 | 1 | MMAO | 90 | 60 | 0.5 | 17 | 35 |

TABLE 4

Analytical Data for run 9–11

| Run | Tm (° C.)[a] | Density (g/cc) | Mw (×10$^{-3}$)[b] | MWD |
|---|---|---|---|---|
| 9 | 132 | 0.952 | 209 | 7.7 |
| 10 | 127 | 0.944 | 84 | 2.3 |
| 11 | 122 | 0.937 | 91 | 2.5 |

[a]Determined by DSC, 2$^{nd}$ heat
[b]Determined by GPC

Example 10

Ethylene/1-hexene Copolymerization Using Compound II

The polymerization run procedures were identical to Example 8 except that the desired amounts of 1-hexene were added. The polymerization results and analytical data are shown in Tables 5 and 6.

TABLE 5

1-Hexene/Ethylene Copolymerization Results using compound II

| Run | [M] μmol | Co-cat | Al/M | 1-Hexene (cc) | Time (h) | Yield (g) | Activity (kg/mmol/h/100 psi C2) |
|---|---|---|---|---|---|---|---|
| 12 | 1 | MMAO | 300 | 0 | 0.5 | 91 | 135 |
| 13 | 1 | MMAO | 300 | 20 | 0.5 | 48 | 79 |
| 14 | 1 | MMAO | 300 | 60 | 1 | 57 | 52 |

TABLE 6

Analytical Data for run 12–14

| Run | Tm (° C.)[a] | Density (g/cc) | Mw (×10$^{-3}$)[b] | MWD |
|---|---|---|---|---|
| 12 | 132 | 0.970 | 30 | 3.0 |
| 13 | 127 | 0.962 | 22 | 2.9 |
| 14 | 124 | 0.954 | 22 | 2.0 |

[a]Determined by DSC, 2$^{nd}$ heat
[b]Determined by GPC

Example 11

Ethylene/Propylene/ENB Terpolymerization

A small glass vial was charged with a magnetic stirbar and a toluene solution of MAO (3 g, 3.15 M) and compound 1 (14 mg, 0.041 mmol) and stirred for 0.5 hour. 500 mL hexane was charged into a 1.0 L stainless-steel reactor (Fluitron®) which had been dried by flowing nitrogen through it while it was held at 100 degrees C. for at least 1 hour (h.), followed by 1 mL of TIBA and 3 mL of ENB (ethylidene norbornene). The reactor was sealed and heated to 60 degrees C., where it was held throughout the remainder of the run by a combination of cold water and steam flowed through the reactor jacket. When the reactor had reached approximately 40 degrees C., the reactor was vented of most of the nitrogen, resealed, and pressurized with a mixture of propylene and ethylene, with the propylene flow made to equal that of ethylene, both measured in L/min. When the reactor had reached ca. 87 psig pressure, the ratio of propylene to ethylene flows was adjusted to 1:3. The reactor temp was then reduced to 50 degrees C. and above catalyst solution (0.5 ml) was injected. When exotherm was over, the temperature was increased to 60 degrees C. and continued for 1 hour (additional 0.5 mL ENB were added at 10 and 20 min into the run) at which point the reactor was vented and the temperature rapidly cooled to room temperature. The polymer was recovered by transfer of the polymer solution to a large glass beaker, to which were added ca. 500 mL of methanol. The recovered polymer was further dried in vacuum oven and weighed 52 g. The polymer contained 9.7 weight % propylene and 6.8 weight % norbornene by NMR. DSC on the polymer revealed a crystallinity of 39.9% on first heat.

Example 12

Ethylene Polymerization Using a Supported Catalyst

Preparation of Supported Catalyst. In the glovebox under nitrogen, a 500 mL 2-neck round-bottom flask was charged with a stirbar, 50 g porous silica (Davison® 955, previously calcined at 250 degrees C.), and 200 hexane. The flask was sealed attached to the vacuum line under nitrogen. In a 250 mL two-necked round-bottom flask were placed a stirbar, 150 g MMAO-3A (Akzo, 1.87 M in heptane), and 0.62 g of 5-[(2-pyridyl)methyl)]-1,2,3,4-tetramethylcyclopentadienyl chromium (III) dichloride (I). This mixture was stirred at RT for about 40 minutes and then cannular transferred into the silica-containing flask in 0.5 h. It was further stirred for 1 additional hour, and the solvent was subsequently removed first by $N_2$ purge and followed by vacuum. Final yield was 82 g of a light purple free-flowing powder. The Kaydol oil catalyst slurry was prepared by adding 0.4 g catalyst in 10 cc oil and sufficiently mixing.

Polymerization Run 500 cc hexane and 1.0 cc Tiba were added into a 1 L stainless-steel reactor (Fluitron®) which had been dried by flowing nitrogen through it while it was held at 100 degrees C. for at least 1 hour (h.), and it was passivated at least for 0.5 h at 50 degrees C. Next, the temperature was raised to 65 degrees C. and overhead pressure was vented off. 2.0 cc of the pre-prepared catalyst oil-slurry was injected and ethylene was quickly introduced into the reaction at 110 psi total pressure, and the temperature was raised to 95 degrees C. The pressure in the reaction was kept constant by supplying ethylene and the temperature was maintained at 95 degrees C. through jack-cooling. After 0.5 hour, the polymerization was stopped and the polymer was taken out from the reactor and dried overnight at ambient temperature to yield 68 g of polymer, activity 73 kg PE/mmol cat. h. 100 psi.

Example 13

Ethylene/Norbornene Copolymerization Using Compound I

Norbornene hexane solution: Norbornene (Aldrich, 11.2 g. 0.12 mol) was dissolved in 100 cc hexane, 14.5 wt %.

The polymerization run procedures were identical to those of Example 8 except that the desired amounts of norbornene hexane solution were added. The polymerization results and analytical data are shown in Table 7.

TABLE 7

Norbornene/Ethylene Copolymerization Results using compound I

| Run | [M] µmol | Co-cat | Al/M | Norbornene (g) | Yield (g) | Activity (kg/mmol/h/ 100 psi C2) | MI2 | Density (g/cc) |
|---|---|---|---|---|---|---|---|---|
| 15 | 1 | MMAO | 300 | 0.4 | 48 | 89 | 1.4 | — |
| 16 | 1 | MMAO | 300 | 1.9 | 59 | 103 | 102 | 0.954 |

Example 14

Ethylene Polymerization Using IBAO as Co-catalyst

Synthesis of 5-[(2-pyridyl)methyl)]-1,2,3,4-tetramethylcyclopentadienyl Chromium (III) dibenzyl (VIII): 5-[(2-pyridyl)methyl)]-1,2,3,4-tetramethylcyclopentadienyl chromium (III) dichloride (1.0 g 2.98 mmol) was suspended in 20 cc toluene and cooled to −78 degrees C., and to this suspension was added benzyl magnesium chloride (Aldrich, 2.0 M, 3.0 cc, 3.0 mmol) drop-wise. The resulting solution was warmed to RT (room temperature) slowly and turned into a brownish-green solution. It was stirred for 12 h. It was then filtered and the solvent was removed by vacuum to result in an oily brown-green solid. It was further washed with hexane (2×10 cc) and dried again under vacuum to yield 1.1 g (85%) of a brown-green solid.

Synthesis of 5-[(2-pyridyl)methyl)]-1,2,3,4-tetramethylcyclopentadienyl chromium (III) dimethyl (compound IX): To a 100 cc Schlenk flask were added $CrCl_3$ (1.58 g, 10 mmol) and ligand 5-[(2-pyridyl)methyl)]-1,2,3,4-tetramethylcyclopentadienyl lithium salt (2.19 g, 10 mmol), and subsequently was added 25 cc THF at RT. A green-blue suspension was observed immediately, and stirring was continued for 5 hours at RT. Then it was cooled to −78 degrees C. MeLi (1.4 M in ether, 14.3 cc, 20 mmol) was added drop-wise and a dark-red solution was observed. It was slowly warmed to RT and stirred for 12 hours. The solvent was removed by vacuum and the resulting solid was extracted with toluene (2×10 cc). Removal of toluene and further wash with hexane (10 cc) resulted in a dark-red solid (2.6 g , 88% based on $CrCl_3$). +APCl/MS spectrum from THF volatilized: [Cr*Me]+, calculated m/e 279.11, [Cr*Me–THF]+, calculated m/e 351.17; [Cr*Me]+, found m/e 278.9, [Cr*Me–THF]+, found m/e351.0.

A hexane stock solution (5.7 mM) was prepared by dissolving 17 mg VIV in 10 cc hexane.

Polymerization Run 500 cc hexane and 1.5 cc IBAO-80 were added into a 1 L stainless-steel reactor (Fluitron®) which had been dried by flowing nitrogen through it while it was held at 100 degrees C. for at least 1 hour (h.), and it was passivated at least for 0.5 h at 50 degrees C. Next, ethylene was introduced into the reaction at 110 psi total pressure and the temperature was allowed to equilibrate at 65 degrees C. The catalyst stock solution (0.15 cc) was injected using a pressure-proof syringe and the temperature was quickly brought to 85 degrees C. The pressure in the reaction was kept constant by supplying ethylene and the temperature was maintained at 85 degrees C. through jacket cooling. After 0.5 hour, the polymerization was stopped and the polymer was taken out from the reactor and dried overnight at ambient temperature to yield 39 g of polymer, activity 92 kg PE/mmol cat. h. 100 psi.

It is significant to note that in the past, where IBAO has been employed as the activating co-catalyst, activity has usually been unsatisfactory. However, in Example 14 herein, surprisingly, activity was good. This is particularly important in view of the fact that IBAO is currently significantly less expensive to obtain or produce than other co-catalyst materials, e.g., MAO and MMAO.

Although the compounds, compositions and processes in accordance with the present invention have been described in connection with preferred embodiments, it will be appreciated by those skilled in the art that modifications not specifically described may be made without departing from the spirit and scope of the invention defined in the following claims.

Each of the U.S. Patents and PCT Publications identified above are hereby expressly incorporated by reference in their entireties.

What is claimed is:

1. A method of making a catalyst, comprising impregnating a catalyst compound on a support material or spray-drying a catalyst compound alone or together with a support material, said catalyst compound having the formula:

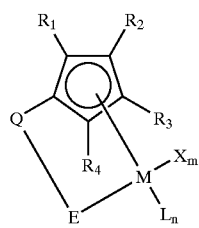

wherein:

$R_1$, $R_2$, $R_3$ and $R_4$ are each independently selected from the group consisting of hydrogen and $C_1$–$C_8$ hydrocarbyl groups, wherein none, one or two pairs of substituents selected from the group consisting of $R_1$, $R_2$, $R_3$ and $R_4$ are linked to form saturated or unsaturated rings;

M is an atom selected from the group consisting of the elements of Groups 4, 5 and 6;

m is 1, 2, 3 or 4;

X is selected from the group consisting of halide elements, $C_1$–$C_8$ hydrocarbyl groups, $C_1$–$C_8$ alkoxy groups, $C_1$–$C_8$ carboxylate groups and $C_1$–$C_8$ carbamate groups;

n is 1, 2 or 3;

L is an organic compound containing at least one lone pair of electrons;

Q is a divalent radical of the formula $TR_5R_6$, wherein T is a Group 14 atom and $R_5$ and $R_6$ are each independently selected from the group consisting of hydrogen and $C_1$–$C_8$ hydrocarbyl groups, and wherein $R_5$ and $R_6$ are not linked or are linked to form a saturated or unsaturated ring;

E is a Lewis basic group having formula (i) or (ii) below:

—C(R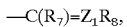)=Z₁R₈, (i)

wherein $R_7$ and $R_8$ are each independently selected from the group consisting of hydrogen and $C_1$–$C_8$ hydrocarbyl groups, and wherein $R_7$ and $R_8$ are not linked or are linked to form a saturated or unsaturated ring; and $Z_1$ is a nitrogen atom or a phosphorus atom, which bonds to M;

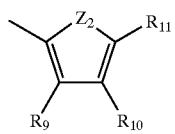

(ii)

wherein:

$Z_2$ is an oxygen atom, a sulphur atom or a selenium atom, which bonds to M; and $R_9$, $R_{10}$ and $R_{11}$ are each independently selected from the group consisting of hydrogen and $C_1$–$C_8$ hydrocarbyl groups, wherein no pair or one pair of substituents selected from $R_9$, $R_{10}$ and $R_{11}$ are linked to form a saturated or unsaturated ring.

2. A catalyst composition comprising:

(A) a catalyst compound having the formula:

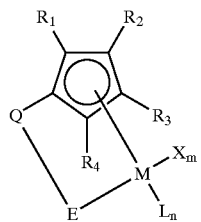

wherein:

$R_1$, $R_2$, $R_3$ and $R_4$ are each independently selected from the group consisting of hydrogen and $C_1$–$C_8$ hydrocarbyl groups, wherein none, one or two pairs of substituents selected from the group consisting of $R_1$, $R_2$, $R_3$ and $R_4$ are linked to form saturated or unsaturated rings;

M is an atom selected from the group consisting of the elements of Groups 4, 5 and 6;

m is 1, 2, 3 or 4;

X is selected from the group consisting of halide elements, $C_1$–$C_8$ hydrocarbyl groups, $C_1$–$C_8$ alkoxy groups, $C_1$–$C_8$ carboxylate groups and $C_1$–$C_8$ carbamate groups;

n is 1, 2 or 3;

L is an organic compound containing at least one lone pair of electrons;

Q is a divalent radical of the formula $TR_5R_6$, wherein T is a Group 14 atom and $R_5$ and $R_6$ are each independently selected from the group consisting of hydrogen and $C_1$–$C_8$ hydrocarbyl groups, and wherein $R_5$ and $R_6$ are not linked or are linked to form a saturated or unsaturated ring;

E is a Lewis basic group having formula (i) or (ii) below:

—C(R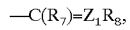)=Z₁R₈, (i)

wherein $R_7$ and $R_8$ are each independently selected from the group consisting of hydrogen and $C_1$–$C_8$ hydrocarbyl groups, and wherein $R_7$ and $R_8$ are not linked or are linked to form a saturated or unsaturated ring; and $Z_1$ is a nitrogen atom or a phosphorus atom, which bonds to M;

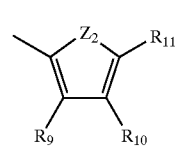

(ii)

wherein:

$Z_2$ is an oxygen atom, a sulphur atom or a selenium atom, which bonds to M; and $R_9$, $R_{10}$ and $R_{11}$ are each independently selected from the group consisting of hydrogen and $C_1$–$C_8$ hydrocarbyl groups, wherein no pair or one pair of substituents selected from $R_9$, $R_{10}$ and $R_{11}$ are linked to form a saturated or unsaturated ring; and (B) an activating co-catalyst, a support material, or both an activating co-catalyst and a support material.

3. The catalyst composition of claim 2, wherein said activating co-catalyst comprises at least one of MAO, MMAO and IBAO.

4. The catalyst composition of claim 2, wherein:

(a) said catalyst compound is impregnated on said support material; or (b) said catalyst compound is dissolved or dispersed in a liquid.

5. The catalyst composition of claim 2, wherein said activating co-catalyst has a formula selected from the group consisting of:

(i) compounds of the formula (a) $M_{co\text{-}cat}R_{12}$, $M_{co\text{-}cat}R_{12}R_{13}$, $M_{co\text{-}cat}R_{12}R_{13}R_{14}$ or $M_{co\text{-}cat}R_{12}R_{13}R_{14}R_{15}$, wherein $M_{co\text{-}cat}$ is a metal selected from the group consisting of alkali metals, alkali earth metals, rare earth metals, aluminum and tin; $R_{12}$, $R_{13}$, $R_{14}$ and $R_{15}$ are each independently selected from the group consisting of hydrogen, $C_1$–$C_8$ hydrocarbyl groups and $C_1$–$C_8$ alkoxy groups, or (b) $(M_{co\text{-}cat}R_{15}O)_p$ $(M_{co\text{-}cat}R_{16}O)_q$, wherein $M_{co\text{-}cat}$ is a metal selected from the group consisting of alkali metals, alkali earth metals, rare earth metals, aluminum and tin; $R_{15}$ and $R_{16}$ of $R_{15}O$ and $R_{16}O$ are each independently selected from the group consisting of hydrogen and $C_1$–$C_8$ hydrocarbyl groups, and p and q are each independently an integer from 1 to 100;

(ii) $MgR_{17}R_{18}$, $ZnR_{17}R_{18}$, $SnR_{17}R_{18}R_{19}R_{20}$, or $LiR_{17}$, wherein $R_{17}$, $R_{18}$, $R_{19}$ and $R_{20}$ are each independently selected from the group consisting of H, $C_1$–$C_8$ hydrocarbyl groups and $C_1$–$C_8$ alkoxy groups; and (iii) non-coordinating anion activators.

6. A process for producing an olefin polymer, which comprises contacting at least one olefin monomer under polymerization conditions with a catalyst composition comprising:

a) a catalyst precursor having the formula:

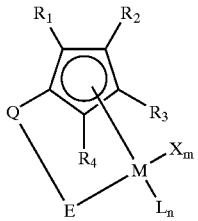

wherein:

$R_1$, $R_2$, $R_3$ and $R_4$ are each independently selected from the group consisting of hydrogen and $C_1$–$C_8$ hydrocarbyl groups, wherein none, one or two pairs of substituents selected from the group consisting of $R_1$, $R_2$, $R_3$ and $R_4$ are linked to form saturated or unsaturated rings;

M is an atom selected from the group consisting of the elements of Groups 4, 5 and 6;

m is 1, 2, 3 or 4;

X is selected from the group consisting of halide elements, $C_1$–$C_8$ hydrocarbyl groups, $C_1$–$C_8$ alkoxy groups, $C_1$–$C_8$ carboxylate groups and $C_1$–$C_8$ carbamate groups;

n is 1, 2 or 3;

L is an organic compound containing at least one lone pair of electrons;

Q is a divalent radical of the formula $TR_5R_6$, wherein T is a Group 14 atom, wherein $R_5$ and $R_6$ are each independently selected from the group consisting of hydrogen and $C_1$–$C_8$ hydrocarbyl groups, and wherein $R_5$ and $R_6$ are not linked or are linked to form a saturated or unsaturated ring;

E is a Lewis basic group having formula (i) or (ii) below:

$$—C(R_7)=Z_1R_8, \quad\quad\quad (i)$$

wherein $R_7$ and $R_8$ are each independently selected from the group consisting of hydrogen and $C_1$–$C_8$ hydrocarbyl groups, and wherein $R_7$ and $R_8$ are not linked or are linked to form a saturated or unsaturated ring; and $Z_1$ is a nitrogen atom or a phosphorus atom, which bonds to M;

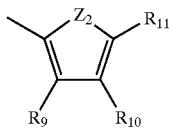

wherein:

$Z_2$ is an oxygen atom, a sulphur atom or a selenium atom, which bonds to M; and $R_9$, $R_{10}$ and $R_{11}$ are each independently selected from the group consisting of hydrogen and $C_1$–$C_8$ hydrocarbyl groups, wherein no pair or one pair of substituents selected from $R_9$, $R_{10}$ and $R_{11}$ are linked to form a saturated or unsaturated ring; and b) an activating co-catalyst.

7. The process of claim 6, wherein said catalyst composition comprises at least two compounds selected from the group consisting of compounds within said formula.

8. The process of claim 6, wherein said process is a suspension reaction process, a solution reaction process, a slurry reaction process or a gas phase reaction process.

9. The process of claim 6, wherein said process is conducted in a batchwise mode, a continuous mode, or a combination thereof.

10. The process of claim 6, wherein said catalyst composition is solid or liquid.

11. The process of claim 6, wherein said at least one olefin monomer is selected from the group consisting of ethylene, linear or branched $C_3$–$C_{20}$ alpha olefins, cyclic olefins, dienes and vinyl unsaturated aromatic compounds.

12. The process of claim 6, wherein said olefin polymer is selected from the group consisting of polyethylene, homopolymers of $C_3$–$C_{20}$ alpha olefins, ethylene/$C_3$–$C_{20}$ alpha olefin copolymers, ethylene/$C_3$–$C_{20}$ alpha olefin/diene terpolymers, ethylene/$C_3$–$C_{20}$ alpha olefin/cyclic olefin terpolymers, polybutadiene and polyisoprene.

13. The process of claim 6, wherein said catalyst precursor is selected from the group consisting of (i) 5-[(2-pyridyl)methyl)]-1,2,3,4-tetramethylcyclopentadienyl chromium (III) dichloride, (ii) 5-[(2-pyridyl)methyl)]-1,2,3,4-tetramethylcyclopentadienyl vanadium (III) dichloride and (iii) 5-[(2-pyridyl)methyl)]-1,2,3,4-tetramethylcyclopentadienyl titanium (III) dichloride.

14. The process of claim 13, wherein said activating co-catalyst comprises at least one of MAO, MMAO and IBAO.

15. The process of claim 6, wherein said contacting at least one olefin monomer with a catalyst composition is carried out in a series of at least two reactors, each said reactor having a unique set of polymerization conditions.

* * * * *